(12) United States Patent
Margosiak et al.

(10) Patent No.: US 7,919,441 B2
(45) Date of Patent: *Apr. 5, 2011

(54) ORDERED LIQUID CRYSTALLINE CLEANSING COMPOSITION WITH SUSPENDED AIR

(75) Inventors: Marion Louise Margosiak, North Wales, PA (US); Rosa Paredes, Shelton, CT (US); Douglas Ryan Eli, Trumbull, CT (US); Jeanne Tighe, River Edge, NJ (US)

(73) Assignee: Unilever Home & Personal Care, division of Conopco, Inc., Greenwich, CT (US)

( * ) Notice: Subject to any disclaimer, the term of this patent is extended or adjusted under 35 U.S.C. 154(b) by 918 days.

This patent is subject to a terminal disclaimer.

(21) Appl. No.: 10/745,074

(22) Filed: Dec. 23, 2003

(65) Prior Publication Data

US 2005/0137101 A1   Jun. 23, 2005

(51) Int. Cl.
   *A61K 7/50* (2006.01)
(52) U.S. Cl. ......... 510/130; 510/156; 510/424; 510/437
(58) Field of Classification Search ................. 510/130, 510/424, 490; 424/70.1
   See application file for complete search history.

(56) References Cited

U.S. PATENT DOCUMENTS

| | | | |
|---|---|---|---|
| 4,824,590 A * | 4/1989 | Roselle .................. | 510/221 |
| 4,870,167 A | 9/1989 | Zody et al. | |
| 5,104,643 A | 4/1992 | Grollier et al. | |
| 6,077,816 A | 6/2000 | Puvvada et al. | |
| 6,194,364 B1 | 2/2001 | Glenn, Jr. | |
| 6,251,954 B1 | 6/2001 | Roulier et al. | |
| 6,426,326 B1 | 7/2002 | Mitra et al. | |
| 6,475,500 B2 * | 11/2002 | Vatter et al. .................. | 424/401 |
| 6,534,457 B2 | 3/2003 | Mitra | |
| 6,605,290 B2 | 8/2003 | Roulier et al. | |
| 2002/0015684 A1 * | 2/2002 | Vatter .................. | 424/70.12 |
| 2003/0072779 A1 | 4/2003 | Sato et al. | |
| 2003/0083210 A1 | 5/2003 | Goldberg et al. | |
| 2003/0171231 A1 | 9/2003 | Shana's et al. | |
| 2003/0180246 A1 * | 9/2003 | Frantz et al. .................. | 424/70.21 |

FOREIGN PATENT DOCUMENTS

| | | | |
|---|---|---|---|
| EP | 0 281 360 B1 | | 9/1988 |
| WO | 98/13022 A1 | | 4/1998 |
| WO | WO 01/19946 | * | 3/2001 |
| WO | 01/96461 | | 12/2001 |
| WO | WO 03/017968 | * | 3/2003 |

OTHER PUBLICATIONS

EP Decision rejecting the opposition (Art. 101(2) EPC), Appl. No. 04 798 122.0-2108 / 1716265, Aug. 5, 2010; 10 pp.
EP (Final) Communication to the parties concerning termination of opposition proceedings, Appl. No. 04 796 122.0-2108/1718268, Nov. 19, 2010, 1 p.
Henkel Opposition letter of Oct. 2, 2008, on EP 1 718 268 B1, 13 pp. (translation).

* cited by examiner

*Primary Examiner* — Necholus Ogden, Jr.
(74) *Attorney, Agent, or Firm* — Alan A. Bornstein

(57) ABSTRACT

An ordered liquid crystalline phase cleansing composition is disclosed that is mild to the skin, contains entrained air and is characterized by excellent sensory and skin feel properties, flow properties and stability.

9 Claims, No Drawings

ORDERED LIQUID CRYSTALLINE CLEANSING COMPOSITION WITH SUSPENDED AIR

BACKGROUND OF THE INVENTION

1. Field of the Invention

The present invention relates to detergent compositions suitable for topical application for cleansing the human body, such as the skin and hair. In particular, it relates to ordered liquid crystalline phase compositions containing suspended air and naturally derived thickeners.

2. Background of the Art

In order to be acceptable to consumers, a liquid personal cleansing product must exhibit good cleaning properties, must exhibit good lathering characteristics, must be mild to the skin (not cause drying or irritation) and preferably have user desired product application and skin feel characteristics.

The majority of prior art liquid cleansing products contain polymers, long-chain unneutralized fatty acids (e.g. C16-C18) or oils as thickeners to increase product viscosity. Although these materials might produce the desired viscosity, they structure the product such that its kinetics of dispersion is slow where the lather is slow to build or slow to rinse off. Furthermore these products evince a heavy or slimy feel when applied to the skin or hair. Surprisingly it has been found that the use of an ordered liquid crystalline phase cleansing composition containing entrained air combined with naturally derived water soluble or dispersible thickeners derived from saccharides gums, proteins, cellulose clays and blends and derivatives thereof provides a light, airy, soufflé or foam-like appearance along with a unique sensory feel and flowability or spreadability when combined with hydrophobic emollients and mild non-soap anionic surfactants. Furthermore, the inventive composition remains stable when stored under extremes in temperature.

Combinations of surfactants and naturally derived thickeners entrained with suspended air have been disclosed for use in liquid cleansing compositions. For example, U.S. patent Publication 2003/0072779 published on Apr. 17, 2003 discloses a whipped o/w emulsion cleansing soap containing cosmetic. Similarly U.S. Pat. Nos. 6,605,290 and 6,251,954; both issued to Roulier et al. on Aug. 12, 2003 and Jun. 26, 2001 respectively; discloses a substantially aerated cleansing composition having a density of 0.2-0.8 gms/cm3 that includes an associative polymer and an anionic surfactant. However there is no disclosure or suggestion in any of these patents and patent applications of an ordered liquid crystal cleansing composition having entrained air, a non-soap anionic surfactant and specific yield strength properties.

BRIEF DESCRIPTION OF THE INVENTION

In one aspect of the present invention is an ordered liquid crystalline cleansing composition containing:
  a. at least about 1% by wt. of a non-soap anionic surfactant;
  b. at least about 0.1% by wt. of an amphoteric surfactant;
  c. an effective amount of an ordered liquid crystalline phase inducing structurant for inducing liquid crystal structure formation in said cleansing composition;
  d. wherein the density of said cleansing composition is in the range of about 0.5 to 1.2;
  e. a water soluble or dispersible thickening agent selected from proteins, mono, di, oligo and polysaccharides; cellulosic materials, gums, clays, or blends or derivatives thereof; and
  f. a yield point in the range of about 3 to 100 Pascals at 25° C.

DETAILED DESCRIPTION OF THE INVENTION

In one aspect of the invention is an ordered liquid crystalline phase cleansing composition including but not limited to:
  a. at least about 1% (preferably at least about 8%) by wt. of a non-soap anionic surfactant (preferably below a maximum amount of 30% by wt.);
  b. at least about 0.1% (preferably at least about 4%) by wt. of an amphoteric surfactant (preferably below a maximum amount of about 15% by wt.);
  c. an effective amount of an ordered liquid crystalline phase inducing structurant for inducing liquid crystal structure formation in said cleansing composition (preferably in the concentration range of about 0.01% to 15% by wt.);
  d. wherein the density of said cleansing composition is in the range of about 0.5 to 1.2 (preferably about 0.7 to 0.95, more preferably about 0.8 to 0.95);
  e. a water soluble or dispersible thickening agent selected from proteins, mono, di, oligo and polysaccharides; cellulosic materials, gums, clays, or blends or derivatives thereof (preferably selected from Xanthan Gum, Pectin, Gelatine derivatives, Clays (such as Laponite), Protein derivatives, Gellan Gum, Cellulose Gums, and the like.); and
  f. a yield point in the range of about 3 to 100 Pascals at 25° C.

Advantageously the liquid crystalline phase inducing structurant is selected from a C8 to C24 alkenyl or branched alkyl fatty acid or ester thereof with a melting point below 25 C, a C8 to C24 alkenyl or branched alkyl fatty alcohol or ether thereof with melting point below 25 C, a C5 to C12 alkyl fatty acid; and trihydroxystearin. Preferably the volume percent of air in the inventive composition is about 5 to 60% by wt. (preferably about 10% to 35%).

Preferably the inventive cleansing composition includes a cationic skin feel agent (preferably in the concentration range of about 0.01% to 3%; more preferably selected from hydroxypropyl trimonium chloride, polyquarternium-10 or a blend thereof. Advantageously inventive composition further includes a hydrophilic and a hydrophobic emollient (preferably the hydrophilic emollient concentration is greater than about 0.1% (preferably greater than about 2%) and is less than about 20%; and the hydrophobic emollient concentration is greater than about 0.5% (preferably greater than about 5%) and is less than about 30% by wt.; Useful emollients are preferably selected from mono, di and triglyceride oils, polyhydric alcohols, esters and sterols, and the like). More preferably, the inventive composition has a particle size range of the hydrophobic emollient is in the range of about 1 to 1000 microns (preferably in the range of about 10 to 50 microns).

Advantageously, the ratio of the anionic to amphoteric surfactant is in the range of about 10:1 to 1:1 (preferably about 6:1 to 2:1); and the composition has lamellar structure (preferably having a viscosity range of about 30,000 to 400,000 cps at 1 rpm (spindle T-B @ 25° C.). More preferably the pH of the inventive composition is in the range of about 4.5-8.0 (preferably 5.5 to 6.5). In a further embodiment the composition is stable at 50° C. temperature for 14 days using the standard stability method. Advantageously the composition contains less than about 5% (preferably less than about 1%) by wt. of soap.

Surfactants:

Surfactants are an essential component of the inventive cleansing composition. They are compounds that have hydrophobic and hydrophilic portions that act to reduce the surface tension of the aqueous solutions they are dissolved in. Useful surfactants include anionic and amphoteric surfactants and optionally nonionic or cationic surfactants, and blends thereof.

Anionic Surfactants:

The cleansing composition of the present invention contains one or more non-soap anionic detergents. The anionic detergent active which may be used may be aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sulfosuccinates may be monoalkyl sulfosuccinates having the formula:

$$R^4O_2CCH_2CH(SO_3M)CO_2M;\ and$$

amide-MEA sulfosuccinates of the formula;

$$R^4CONHCH_2CH_2O_2CCH_2CH(SO_3M)CO_2M$$

wherein $R^4$ ranges from $C_8$-$C_{22}$ alkyl and M is a solubilizing cation.

Sarcosinates are generally indicated by the formula:

$$R^1CON(CH_3)CH_2CO_2M,$$

wherein $R^1$ ranges from $C_8$-$C_{20}$ alkyl and M is a solubilizing cation.

Taurates are generally identified by formula:

$$R^2CONR^3CH_2CH_2SO_3M$$

wherein $R^2$ ranges from $C_8$-$C_{20}$ alkyl, $R^3$ ranges from $C_1$-$C_4$ alkyl and M is a solubilizing cation.

The inventive cleansing composition contains anionic surfactants, preferably $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

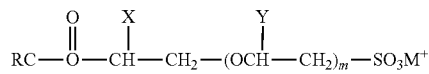

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Amphoteric Surfactants

One or more amphoteric surfactants are used in this invention. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

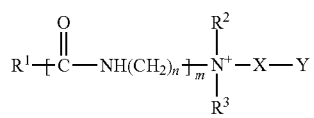

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—

Suitable amphoteric surfactants within the above general formula include simple betaines of formula:

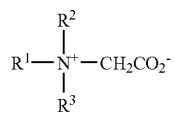

and amido betaines of formula:

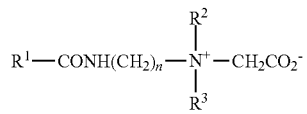

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

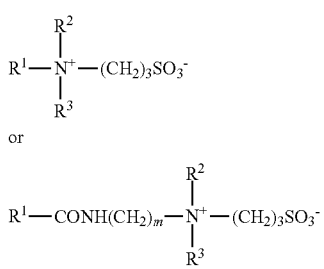

or

where m is 2 or 3, or variants of these in which —(CH$_2$)$_3$SO$_3^-$ is replaced by $$—CH_2\overset{\underset{|}{OH}}{C}HCH_2SO_3^-$$

In these formulae R$^1$, R$^2$ and R$^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

Nonionic Surfactants

One or more nonionic surfactants may also be used in the cleansing composition of the present invention.

The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl (C$_6$-C$_{22}$) phenols ethylene oxide condensates, the condensation products of aliphatic (C$_8$-C$_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference. Nonionic surfactants are preferably used at minimum levels of about 0.1% and maximum levels of about 25%.

Cationic Skin Conditioning Agents

An optional component in compositions according to the invention is a cationic skin feel agent or polymer, such as for example cationic celluloses. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Particularly preferred cationic polymers are JAGUAR C13S, JAGUAR C15, JAGUAR C17 and JAGUAR C16 and JAGUAR C162, especially Jaguar C13S. Other cationic skin feel agents known in the art may be used provided that they are compatible with the inventive formulation. Cationic polymers are preferably used at minimum levels of about 0.01% and maximum levels of about 3.0%.

Cationic Surfactants

One or more cationic surfactants may also be used in the cleansing composition. Cationic surfactants are preferably used at minimum levels of about 0.1% and maximum levels of about 25%.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry & Berch, both of which are also incorporated into the subject application by reference.

Thickeners

One or more thickeners are used in the invention. These may be of natural or synthetic origin or of derivatives or blends thereof. Some examples of useful natural thickeners are water soluble or dispersible proteins, mono, di, oligo and polysaccharides; cellulosic materials, gums, clays, or blends or water soluble or dispersible derivatives thereof and the like. Some examples of useful synthetic thickeners are polyethylene glycol, polyvinyl pyrrolidone, polyvinyl acetate, acrylate homopolymers and copolymers, methacrylate homopolymers and copolymers, carboxymethyl and ethyl cellulose and the like. A particularly suitable type of thickener is gelatine. Thickeners are preferably used at minimum levels of about 0.05% and maximum levels of about 15%.

In addition, the inventive cleansing composition of the invention may include 0 to about 15% by wt. optional ingredients as follows: perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, TiO$_2$, EGMS (ethylene glycol monostearate) or Lytron 621 (Styrene/Acrylate copolymer) and the like; all of which are useful in enhancing the appearance or cosmetic properties of the product.

The compositions may further comprise antimicrobials such as 2-hydroxy-4,2',4' trichlorodiphenylether (DP300);

preservatives such as dimethyloldimethylhydantoin (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and the like may be used advantageously in amounts of about 0.01% or higher if appropriate.

Emollients:

Hydrophillic emollients or humectants such as polyhydric alcohols, e.g. glycerine and propylene glycol, and the like; and polyols such as the polyethylene glycols listed below and the like may be used.

Polyox WSR-205 PEG 14M,
Polyox WSR-N-60K PEG 45M, or
Polyox WSR-N-750 PEG 7M.

A blend of a hydrophobic and hydrophilic emollients may be advantageously used. Preferably, hydrophobic emollients are used in excess of hydrophilic emollients in the inventive cleansing composition. Most preferably one or more hydrophobic emollients are used alone. Hydrophobic emollients are preferably present in a concentration greater than about 1, 2, 3, 5, 6, 7, or 10% by weight. The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Useful emollients include the following:
(a) silicone oils and modifications thereof such as linear and cyclic polydimethylsiloxanes; amino, alkyl, alkylaryl, and aryl silicone oils;
(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;
(c) waxes such as carnauba, spermaceti, beeswax, lanolin, and derivatives thereof;
(d) hydrophobic and hydrophillic plant extracts;
(e) hydrocarbons such as liquid paraffins, vaseline, microcrystalline wax, ceresin, squalene, pristan and mineral oil;
(f) higher fatty acids such as lauric, myristic, palmitic, stearic, behenic, oleic, linoleic, linolenic, lanolic, isostearic, arachidonic and poly unsaturated fatty acids (PUFA);
(g) higher alcohols such as lauryl, cetyl, stearyl, oleyl, behenyl, cholesterol and 2-hexydecanol alcohol;
(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;
(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;
(j) lipids such as cholesterol, ceramides, sucrose esters and pseudo-ceramides as described in European Patent Specification No. 556,957;
(k) vitamins, minerals, and skin nutrients such as milk, vitamins A, E, and K; vitamin alkyl esters, including vitamin C alkyl esters; magnesium, calcium, copper, zinc and other metallic components;
(l) sunscreens such as octyl methoxyl cinnamate (Parsol MCX) and butyl methoxy benzoylmethane (Parsol 1789);
(m) phospholipids;
(n) antiaging compounds such as alpha hydroxy acids, beta hydroxy acids; and
(o) mixtures of any of the foregoing components, and the like.

Preferred emollients are selected from triglyceride oils, mineral oils, petrolatum, and mixtures thereof. Further preferred emollients are triglycerides such as sunflower seed oil.

Ordered Liquid Crystalline Compositions:

The inventive cleansing composition possesses ordered liquid crystalline microstructure, preferably lamellar microstructure structure. The rheological behavior of all surfactant solutions, including liquid cleansing solutions, is strongly dependent on the microstructure, i.e., the shape and concentration of micelles or other self-assembled structures in solution.

When there is sufficient surfactant to form micelles (concentrations above the critical micelle concentration or CMC), for example, spherical, cylindrical (rod-like or discoidal), spherocylindrical or ellipsoidal micelles may form. As surfactant concentration increases, ordered liquid crystalline phases such as lamellar phase, hexagonal phase, cubic phase or L3 sponge phase may form. The lamellar phase, for example, consists of alternating surfactant bilayers and water layers. These layers are not generally flat but fold to form submicron spherical onion like structures called vesicles or liposomes. The hexagonal phase, on the other hand, consists of long cylindrical micelles arranged in a hexagonal lattice. In general, the microstructure of most personal care products consist of either spherical micelles; rod micelles; or a lamellar dispersion.

As noted above, micelles may be spherical or rod-like. Formulations having spherical micelles tend to have a low viscosity and exhibit Newtonian shear behavior (i.e., viscosity stays constant as a function of shear rate; thus, if easy pouring of product is desired, the solution is less viscous and, as a consequence, it doesn't suspend as well). In these systems, the viscosity increases linearly with surfactant concentration.

Rod micellar solutions are more viscous because movement of the longer micelles is restricted. At a critical shear rate, the micelles align and the solution becomes shear thinning. Addition of salts increases the size of the rod micelles thereof increasing zero shear viscosity (i.e., viscosity when sitting in bottle) which helps suspend particles but also increases critical shear rate (point at which product becomes shear thinning; higher critical shear rates means product is more difficult to pour).

Lamellar dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

In formulating liquid cleansing compositions, therefore, there is the choice of using rod-micellar solutions (whose zero shear viscosity, e.g., suspending ability, is not very good and/or are not very shear thinning); or lamellar dispersions (with higher zero shear viscosity, e.g. better suspending, and yet are very shear thinning). Such lamellar compositions are characterized by high zero shear viscosity (good for suspending and/or structuring) while simultaneously being very shear thinning such that they readily dispense in pouring. Such compositions possess a "heaping", lotion-like appearance which convey signals of enhanced moisturization.

When rod-micellar solutions are used, they also often require the use of external structurants to enhance viscosity and to suspend particles (again, because they have lower zero shear viscosity than lamellar phase solutions). For this, carbomers and clays are often used. At higher shear rates (as in product dispensing, application of product to body, or rubbing with hands), since the rod-micellar solutions are less shear thinning, the viscosity of the solution stays high and the product can be stringy and thick. Lamellar dispersion based products, having higher zero shear viscosity, can more readily suspend emollients and are typically more creamy. In general, lamellar phase compositions are easy to identify by their characteristic focal conic shape and oily streak texture while hexagonal phase exhibits angular fan-like texture. In contrast, micellar phases are optically isotropic.

It should be understood that lamellar phases may be formed in a wide variety of surfactant systems using a wide variety of lamellar phase "inducers" as described, for example, in U.S. Pat. No. 5,952,286 issued to Puvvada, et al., on Sep. 14, 1999. Generally, the transition from micelle to lamellar phase are functions of effective average area of headgroup of the surfactant, the length of the extended tail, and the volume of tail. Using branched surfactants or surfactants with smaller headgroups or bulky tails are also effective ways of inducing transitions from rod micellar to lamellar.

One way of characterizing ordered liquid crystalline dispersions include measuring viscosity at low shear rate (using for example a Stress Rheometer) when additional inducer (e.g., oleic acid or isostearic acid) is used. At higher amounts of inducer, the low shear viscosity will significantly increase.

Another way of measuring ordered liquid crystalline dispersions is using freeze fracture electron microscopy. Micrographs generally will show ordered liquid crystalline microstructure and close packed organization of the lamellar droplets (generally in size range of about 2 microns).

The inventive ordered liquid crystalline-isotropic composition preferably has a low shear viscosity in the range of about 30,000 to about 400,000 centipoises (cps) measured at 0.5 RPM using T-bar spindle A using the procedure described below. More preferably the viscosity range is about 30,000 to about 100,000 cps.

The invention will now be described in greater detail by way of the following non-limiting examples. The examples are for illustrative purposes only and not intended to limit the invention in any way.

Except in the examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

EXAMPLE 1

Six inventive compositions (1, 2, 4, and 6-8) were prepared and compared to two comparative compositions 3 and 5 according Table 1 using the processing methods described below. The specific gravity of the inventive compositions was approx. 0.85.

TABLE 1

| Ingredients | 1 % wt/wt | 2 % wt/wt | 3 % wt/wt | 4 % wt/wt | 5 % wt/wt | 6 % wt/wt | 7 % wt/wt | 8 % wt/wt |
|---|---|---|---|---|---|---|---|---|
| Sodium Laureth Sulfate | 8 | | 9 | 8 | 9 | | 10 | |
| Cocamidopropyl betaine | | 4 | 4 | 4 | 4 | 5 | | 5 |
| Sodium Lauryl Amphoacetate | 4 | | | | | | 5 | |
| Cocamide MEA | 2 | | | | | 3.44 | 2 | 2.96 |
| Ammonium Laureth Sulfate | | 3.51 | | | | 4.4 | | 4.4 |
| Ammonium Lauryl Sulfate | | 4.5 | | | | 5.62 | | 5.62 |
| Acrylates Copolymer | | | | | 3 | | 5 | |
| Sunflower Seed Oil | 4 | 4 | | 4 | | 5 | | 5 |
| Gelatin | 1.2 | 1.2 | 5 | 1.2 | | 1.2 | 1.2 | 1.5 |
| Lauric Acid | 2.24 | 2.8 | | 3 | | 2.8 | 2.8 | 2.8 |
| Cetyl Alcohol and Acetylated Lanolin Alcohol | 0.8 | 0.8 | | 0.4 | | 1 | 1 | 1 |
| Glycerin | 1 | 1 | | 1 | | 2 | 2 | 2 |
| Hydroxypropyl Trimonium Chloride | 0.5 | 0.5 | | 0.5 | | 0.5 | 0.5. | 0.5 |
| Ammonium Sulfate | | | | | | | | |
| Sodium Hydroxide | | | 0.5 | | 0.5 | | | |
| Citic Acid | 0.8 | 0.4 | | | | | 1 | 1 |
| Tetrasodium EDTA | 0.02 | 0.02 | 0.02 | 0.02 | 0.02 | 0.02 | 0.02 | 0.02 |
| Etidronic Acid | 0.02 | 0.02 | 0.02 | 0.02 | 0.02 | 0.02 | 0.02 | 0.02 |
| DMDM Hydantoin + IPBC | | | | | | 0.02 | 0.22 | |
| Methylchloroisothiazolinone, Methylisothiazolinone | 0.0003 | 0.0003 | 0.0003 | 0.0003 | 0.0003 | 0.0003 | | 0.0003 |
| Fragrance | 1 | 1 | 1 | 1 | 1 | 1 | 1 | 1 |
| Water | q.s. to 100 | q.s. to 100 | q.s. to 100 | q.s. to 100 | q.s. to 100 | q.s. to 100 | q.s. to 100 | q.s. to 100 |
| Product Type | Lamellar | Lamellar | Isotropic | Lamellar | Isotropic | Lamellar | Lamellar | Lamellar |

TABLE 1-continued

| Ingredients | 1 % wt/wt | 2 % wt/wt | 3 % wt/wt | 4 % wt/wt | 5 % wt/wt | 6 % wt/wt | 7 % wt/wt | 8 % wt/wt |
|---|---|---|---|---|---|---|---|---|
| Processing Method | 2 | 4 | 3 | 4 | 1 | 5 | 2 | 5 |
| Inventive | YES | YES | NO | YES | NO | YES | YES | YES |

PROCESSING METHODS FOR EXAMPLE 1

Processing method no. 1 Charge kettle with initial water and start to mix. Add Acrylates Copolymer and increase mixing speed until a vortex is formed. Add the anionic surfactant and mix. Add the amphoteric surfactant and mix. Add preservative, tetrasodium EDTA, and etrdronic acid. Adjust pH with caustic to approximately 6.0 to 7.0. Add Fragrance with mixing. Mix batch with a high shear mixer for 2 minutes to incorporate air, or until the batch volume doubles.

Processing method no. 2 Charge kettle with Amphoacetate and heat to 73 C with mixing. Add gelatin with mixing and mix for 10 minutes. Add Cocamide MEA and mix for 5 minutes or until dissolved. Add anionic surfactant with mixing. Heat a side vessel of water to 55 C and add to the main batch. Add citric acid and mix for 10 minutes. Add oil, fatty acid, and alcohols. Mix until homogeneous. With agitation, add glycerin and cationic polymer to the main batch. Cool to 30 C. Add preservative, tetrasodium EDTA, and etrdronic acid. Add fragrance with mixing. Mix batch with a high shear mixer for 2 minutes to incorporate air, or until the batch volume doubles.

Processing method no. 3 Charge kettle with initial water. With mixing heat to 160 F. Increase mixing speed until a vortex is formed. Add Gelatin. Add the anionic surfactant and mix. Add the amphoteric surfactant and mix. Add preservative, tetrasodium EDTA, and etidronic acid. Mix for 10 minutes. Add Fragrance with mixing and mix 15 minutes. Adjust pH with caustic to approximately 6.0 to 7.0. Mix batch with a high shear mixer for 2 minutes to incorporate air, or until the batch volume doubles.

Processing method no. 4 Charge kettle with initial water and heat to 73 C with mixing. Add gelatin with mixing and mix for 10 minutes. Add Amphoteric surfactance and mix. Add anionic surfactants and mix for 10 minutes. Add citric acid and mix for 10 minutes. Add oil, fatty acid, and alcohols. Mix until homogeneous. With agitation, add glycerin and cationic polymer to the main batch. Cool to 55 C. Add preservative, tetrasodium EDTA, and editronic acid. Add fragrance with mixing. Mix batch with a high shear mixer for 2 minutes to incorporate air, or until the batch volume doubles.

Processing method no. 5 Charge kettle with amphoteric surfactant and heat with mixing to 73 C. Add Cocamide MEA and mix until melted. Add anionic surfactant with mixing and mix for 15 minutes at 73 C. Heat a side vessel of water to 55 C, add gelatin and mix until homogeneous. Add to the main batch. With agitation, add glycerin and cationic polymer to the main batch. Cool to 30 C. Add preservative, tetrasodium EDTA, and etrdronic acid. Add fragrance with mixing. Mix batch with a high shear mixer for 2 minutes to incorporate air, or until the batch volume doubles.

EXAMPLE 2

Four inventive compositions according to Tables 2-5 were prepared and compared to a comparative composition according to Table 6 using the processing method described below. Aeration content, viscosity, and yield point are provided (measured as described below) along with a description of the qualitative form of the composition.

TABLE 2

| inventive Composition 1-33 | |
|---|---|
| INCI Ingredient | % active |
| Water | qs |
| Gelatine (1) | 1.5 |
| Cocamidopropyl Betaine (2) | 5 |
| Cocamide MEA (3) | 2.96 |
| Ammonium Lauryl Sulfate | 4.39 |
| Ammonium Laureth Sulfate | 5.62 |
| PEG-5 Cocamide | 0.48 |
| Sunflower Seed Oil | 5 |
| Lauric Acid (4) | 2.8 |
| Acetylated Lanolin Alcohol (5) | 1 |
| Glycerine | 2 |
| Guar Hydroxypropyl trimonium chloride (6) | 0.5 |
| tetrasodium EDTA (7) | 0.02 |
| Etidronic Acid | 0.02 |
| Kathon CG | 0.0003 |
| perfume | 1 |
| 30% | Aeration |
| 330,000 cps at_C | Viscosity |
| 67.3 Pascals | Yield Point |

Form: Very stiff, holds air well, does not flow from bottle or tube Requires tub type dispenser

TABLE 3

| inventive Composition 1-89 | |
|---|---|
| INCI Ingredient | % active |
| Water | qs |
| Gelatine | 1.5 |
| Cocamidopropyl Betaine | 5 |
| Cocamide MEA | 2.96 |
| Ammonium Lauryl Sulfate | 4.39 |
| Ammonium Laureth Sulfate | 5.62 |
| PEG-5 Cocamide | 0.48 |
| Sunflower Seed Oil | 5 |
| Lauric Acid | 2.8 |
| Acetylated Lanolin Alcohol | 1 |
| Glycerine | 2 |
| Guar Hydroxypropyl trimonium chloride | 0.5 |
| tetrasodium EDTA | 0.02 |
| Etidronic Acid | 0.02 |
| Kathon CG | 0.0003 |
| perfume | 1 |
| 15% | Aeration |
| 51,000 | Viscosity |
| 11.5 | Yield Point |

Form: soufflé-like, hold air and flows well

TABLE 4

| inventive Composition 1-92 | |
|---|---|
| INCI Ingredient | % active |
| Water | qs |
| Gelatine | 1.5 |
| Cocamidopropyl Betaine | 5 |
| Cocamide MEA | 2.96 |
| Ammonium Lauryl Sulfate | 4.39 |
| Ammonium Laureth Sulfate | 5.62 |
| PEG-5 Cocamide | 0.48 |
| Sunflower Seed Oil | 5 |
| Lauric Acid | 2 |
| Acetylated Lanolin Alcohol | 1 |
| Glycerine | 2 |
| Guar Hydroxypropyl trimonium chloride | 0.5 |
| tetrasodium EDTA | 0.02 |
| Etidronic Acid | 0.02 |
| Kathon CG | 0.0003 |
| perfume | 1 |
| 15% | Aeration |
| 33,000 | Viscosity |
| 10.1 | Yield Point |

Form: very good flow properties, good stability

TABLE 5

| inventive Composition 1-113 | |
|---|---|
| INCI Ingredient | % active |
| Water | qs |
| Gelatine | 1.25 |
| Cocamidopropyl Betaine | 4 |
| Cocamide MEA | 1.26 |
| Ammonium Lauryl Sulfate | 3.47 |
| Ammonium Laureth Sulfate | 4.44 |
| PEG-5 Cocamide | 0.38 |
| Sunflower Seed Oil | 4 |
| Lauric Acid | 3 |
| Acetylated Lanolin Alcohol | 0.25 |
| Glycerine | 1 |
| Guar Hydroxypropyl trimonium chloride | 0.2 |
| tetrasodium EDTA | 0.02 |
| Etidronic Acid | 0.02 |
| Kathon CG | 0.0003 |
| perfume | 1 |
| 15% | Aeration |
| 51,500 | Viscosity |
| 14.6 | Yield Point |

Form: Good stability but did not flow well enough for use in bottle

TABLE 6

| Comparative Composition 1-117 | |
|---|---|
| INCI Ingredient | % active |
| Water | qs |
| Gelatine | 1.5 |
| Cocamidopropyl Betaine | 4 |
| Cocamide MEA | 1.26 |
| Ammonium Lauryl Sulfate | 3.47 |
| Ammonium Laureth Sulfate | 4.44 |
| PEG-5 Cocamide | 0.38 |
| Sunflower Seed Oil | 4 |

TABLE 6-continued

| Comparative Composition 1-117 | |
|---|---|
| INCI Ingredient | % active |
| Lauric Acid | 3 |
| Glycerine | 1.5 |
| Guar Hydroxypropyl trimonium chloride | 0.4 |
| tetrasodium EDTA | 0.02 |
| Etidronic Acid | 0.02 |
| Kathon CG | 0.0003 |
| perfume | 1 |
| 15% | Aeration |
| 39,500 | Viscosity |
| 2.7 | Yield Point |

Form: does not hold entrained air well

Notes:
1. Gelatin 275 Bloom
2. Tegobetain F
3. Mackamide CMA
4. Prifrac 2922
5. Crodalan LA
6. Jaguar C13S
7. Versene 100XL @ 39%

PROCESS DETAILS FOR EXAMPLE 2

| Step | Procedure |
|---|---|
| 1 | Add water to main vessel |
| 2 | Add gelatine to main and begin heating to 73 degrees C. |
| 3 | Add Betaine to main while heating |
| 4 | Add Cocamide MEA to main while heating |
| 5 | add ALS, ALES, and PEG-5 Cocamide while heating |
| 6 | Bring Main to 55 degrees C. and mix until uniform |
| 7 | In a separate vessel premix Sunflower Oil, lauric acid, and acetylated lanonlin alcohol with heating until uniform (73 C.) |
| 8 | Add sunflower oil mix from previous step to main batch when uniform and at 73 degrees C. |
| 9 | In another vessel premix glycerine and Hydroxypropyl trimonium chloride |
| 10 | Add glycerin mix to main batch |
| 11 | Maintian temperature at 73 degrees C. for 30 minutes |
| 12 | Begin cooling to 25 C. |
| 13 | Add Kathon at 46 C. or lower |
| 14 | Add EDTA and EHDP |
| 15 | Add fragrance at 30 C. |
| 16 | When all materials have been added, whip the product using a homogenizer (rpm and time will depend on batch size and viscosity). Homogenize uniformly and until the desired level of air has been incorporated. |

Methods:

Procedure for Yield Stress Measurement

Yield stress, or yield point, is the amount of force required to initiate flow of a semi-solid. A controlled stress rheometer was programmed to increase the amount of shear stress linearly from 1 Pascal until the material's viscosity decreased (started to flow). The amount of force was noted and recorded. The temperature was maintained at a constant 25° C.

Instrument: Carri-Med CSL 100 controlled shear stress rheometer.

Geometry: Plate and cone (4 cm, 2 degree).

Temperature: 25° C.

Stress ramp: from 1-50 Pascals linearly in 2 minutes.

Viscosity Measurement

Fill a wide mouth jar (~60 mm wide ~70 mm tall) with product at 25 degrees C.

Using a descending Brookfield DV-II+ viscometer, place the heliopath spindle at the surface of the product spindle selection is based on product viscosity. For thinner Products (100,000 cps and lower) TA at 2 rpm is used. If the viscosity goes above 100,000 cps the spindle is T-B and the speed remains 2 rpm.

The spindle motor and descending motor are turned on simultaneously.

After 2 minutes the dial reading is the measured viscosity.

Standard Stability Method:

Samples are held at room temperature in sealed containers for at least 70 days and at elevated temperature (50° C.) for fourteen (14) days. "Stability" is therefore defined as used herein as the ability of the inventive composition to maintain a homogenous physical appearance or show no more than a 20% decrease in viscosity under such combination of time and temperature.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. An ordered liquid crystalline phase cleansing composition comprising:
   a. at least about 1% by wt. of a non-soap anionic surfactant;
   b. at least about 0.1% by wt. of an amphoteric surfactant;
   c. an effective amount of an ordered liquid crystalline phase inducing structurant for inducing liquid crystal structure formation in said cleansing composition;
   d. wherein the density of said cleansing composition is in the range of about 0.5 to 1.2 gms/cm$^3$ at 25° C.;
   e. a water soluble or dispersible thickening agent selected from proteins, mono, di, oligo and polysaccharides; cellulosic materials, gums, clays, or blends or derivatives thereof;
   f. a yield point in the range of about 3 to 100 Pascals at 25° C.;
   g. wherein the volume percent of air suspended in the composition is about 10 to 60%; and
   h. wherein the composition is stable at 50° C. temperature for 14 days without noticeable phase separation or a decrease in viscosity of more than about 20% or both.

2. The cleansing composition of claim 1 wherein the liquid crystalline phase inducing structurant is selected from a C8 to C24 alkenyl or branched alkyl fatty acid or ester thereof with a melting point below 25 C, a C8 to C24 alkenyl or branched alkyl fatty alcohol or ether thereof with melting point below 25 C, a C5 to C12 alkyl fatty acid; and trihydroxystearin.

3. The cleansing composition of claim 1 further comprising a cationic skin feel agent.

4. The cleansing composition of claim 1 further comprising a hydrophilic and a hydrophobic emollient.

5. The cleansing composition of claim 4 wherein the particle size range of the hydrophobic emollient is in the range of about 1 to 1000 microns.

6. The cleansing composition of claim 1 wherein the ratio of the anionic to amphoteric surfactant is in the range of about 10:1 to 1:1.

7. The cleansing composition of claim 1 wherein the composition has lamellar structure.

8. The cleansing composition of claim 1 where the pH of the composition is in the range of about 4.5-8.0.

9. The cleansing composition of claim 1 wherein the composition contains less than about 5% by wt. of soap.

\* \* \* \* \*